United States Patent
Mansour et al.

(10) Patent No.: US 6,649,756 B2
(45) Date of Patent: Nov. 18, 2003

(54) PROCESS IMPROVEMENT IN THE PREPARATION OF (4R, 5S, 6S)-3-[[(2R,3R)-2-[[[(S)-2-AMINO-3-METHYL-1-OXOBUTYL]AMINO]METHYL]TETRAHYDRO-3-FURANYL]THIO]-6-[(R)-1-HYDROXYETHYL]-4-METHYL-7-OXO-1-AZABICYCLO[3.2.0]HEPT-2-ENE-2-CARBOXYLIC ACID

(75) Inventors: Tarek Mansour, New City, NY (US); Phaik-Eng Sum, Pomona, NY (US); Yang-I Lin, Tappan, NY (US); Zhong Li, Congers, NY (US)

(73) Assignee: Wyeth, Five Giralda Farms, Madison, NJ (US)

( * ) Notice: Subject to any disclaimer, the term of this patent is extended or adjusted under 35 U.S.C. 154(b) by 0 days.

(21) Appl. No.: 09/901,335

(22) Filed: Jul. 9, 2001

(65) Prior Publication Data

US 2002/0128283 A1 Sep. 12, 2002

Related U.S. Application Data

(60) Provisional application No. 60/217,925, filed on Jul. 13, 2000.

(51) Int. Cl.[7] .............................................. C07D 477/20
(52) U.S. Cl. ........................................................ 540/350
(58) Field of Search ........................................... 540/350

(56) References Cited

U.S. PATENT DOCUMENTS

| | | | | |
|---|---|---|---|---|
| 4,201,782 A | * | 5/1980 | Narisada et al. | 514/210.08 |
| 4,254,029 A | * | 3/1981 | Kaspi et al. | 540/224 |
| 5,093,464 A | * | 3/1992 | Yoon et al. | 528/329.1 |
| 5,602,118 A | | 2/1997 | Lin et al. | |
| 6,436,921 B1 | * | 8/2002 | Park et al. | 540/350 |

FOREIGN PATENT DOCUMENTS

WO 9914218 3/1999

OTHER PUBLICATIONS

Tetrahedron Letters, 39, (1998), Amar S. Prashad et al.p. 7035–7038.
Japanese Kokai Application Patent No. Hei 7[1995]–70139.
Japanese Kokai Application Patent No. Hei 7[1995]–70139 (English Translation).
Remington's Pharmaceutical Sciences (1990) 18th Edition, A. R. Gennaro, p. 1565–1567.
J.Amer.Chem. Soc., 100:25, (1978),L.D. Cama and B.G. Christensen p. 8006–8007.

* cited by examiner

*Primary Examiner*—Mark L. Berch
(74) *Attorney, Agent, or Firm*—Daniel B. Moran; Thomas S. Szatkowski

(57) ABSTRACT

The invention is a process improvement for producing the carbapenem antibacterial agent (4R, 5S, 6S)-3-[[2R,3R)-2-[[[(S)-2-amino-3-methyl-1-oxobutyl]amino]methyl]tetrahydro-3-furanyl]thio]-6-[R)-1-hydroxyethyl]-4-methyl-7-oxo-1-azabicyclo[3.2.0]hept-2-ene-2-carboxylic acid by hydrogenation of 4-nitrobenzyl (4R,5S,6S)-6-[(1R)-1-hydroxyethyl]-4-methyl-3-{[2R,3R)-2-({[(2S)-3-methyl-2-({[4-nitrobenzyl)oxy]carbonyl}amino)butanoyl]amino}methyl)-tetrahydrofuran-3-yl]thio}-7-oxo-1-azabicyclo[3.2.0]hept-2-ene-2-carboxylate in a biphasic solvent mixture comprising a water portion and an organic solvent portion, not containing an acid acceptor. The water portion is separated from the organic solvent portion and (4R,5S,6S)-3-[[(2R,3R)-2-[[[(S)-2-amino-3-methyl-1-oxobutyl]amino]methyl]tetrahydro-3-furanyl]thio]-6-[R-hydroxyethyl]-4-methyl-7-oxo-1-azabicyclo[3.2.0]hept-2-ene-2-carboxylic acid is isolated from the separated water portion by lyophilization or reverse osmosis.

16 Claims, No Drawings

PROCESS IMPROVEMENT IN THE PREPARATION OF (4R, 5S, 6S)-3-[[(2R,3R)-2-[[[(S)-2-AMINO-3-METHYL-1-OXOBUTYL]AMINO]METHYL]TETRAHYDRO-3-FURANYL]THIO]-6-[(R)-1-HYDROXYETHYL]-4-METHYL-7-OXO-1-AZABICYCLO[3.2.0]HEPT-2-ENE-2-CARBOXYLIC ACID

CROSS REFERENCE TO RELATED APPLICATION

This application claims benefit of U.S. Provisional Appl. No. 60/217,925, which was filed Jul. 13, 2000. This application is herein incorporated by reference.

BACKGROUND OF INVENTION

The invention is concerned with an improved process for the preparation of (4R, 5S, 6S)-3-[[(2R,3R)-2-[[[(S)-2-amino-3-methyl-1-oxobutyl]amino]methyl]-tetrahydro-3-furanyl]thio]-6-[(R)-1-hydroxyethyl]-4-methyl-7-oxo-1-azabicyclo[3.2.0]hept-2-ene-2-carboxylic acid, a member of the carbapenem class of compounds, which is useful as an antibacterial agent.

PRIOR ART

In general it is well known in the art that carbapenem compounds are very difficult to produce because, inter alia, their sensitivity to heat and purification procedures results in low yields and which further requires isolation by chromatography. Synthetic methods to produce carbapenems require the use of protecting groups, which when removed, produce not only the carbapenem product, but additionally unwanted contaminates. The removal of additional contaminates, produced by the removal of protecting groups often requires the use of chromatography in order to separate and purify the labile carbapenem. Typically, protecting groups such as p-nitrobenzyl (PNB) and p-nitrobenzyloxycarbonyl (PNZ) have been used in the preparation of carbapenem compounds as shown for example by Amar S. Prashad, Nancy Vlahos, Paul Fabio and Gregg B. Feigelson, Tetrahedron Letters, 39, (1998), 7035–7038 and L. D. Cama and B. G. Christensen, J. Am. Chem. Soc., 100, 8006(1978). However, following removal of protection groups (PNB) and (PNZ), chromatography is required to separate and isolate the carbapenem product, often in low yield, from contaminates. While production of carbapenems typically proceeds via removal of a single ester protecting group (PNB) in the presence of a buffer, the separation and isolation of a carbapenem from unwanted contaminates is difficult and is increasingly more difficult when two or more protecting groups, (PNB) and (PNZ) are simultaneously removed.

Japanese Kokai Application Patent No. Hei 7[1995]-70137 teaches the removal of a single (PNB) ester protecting group from 2-(mono- or disubstituted-6,7-dihydro-5H-pyrazo[1,2-a]pyrazolium-6-yl)thiocarbapenems, of the formula

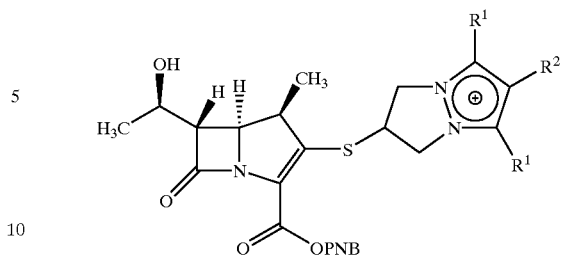

by hydrogenation in the presence of palladium-on-carbon. Removal of the (PNB) group by hydrogenation is carried out in aqueous acetic acid buffer at pH 5.5, or morpholinopropanesulfonic acid-sodium hydroxide buffer solution at pH 5.5, or phosphate buffer at pH 5.5, or dipotassium phosphate, or sodium hydrogen carbonate in solvent mixtures which include tetrahydrofuran-water, tetrahydrofuran-water-ethanol, dioxane-water, dioxane-water-ethanol and butanol-water to afford the 2-(mono- or disubstituted-6,7-dihydro-5H-pyrazo[1,2-a]pyrazolium-6-yl)thiocarbapenems. The application teaches ion-exchange and chromatographic separation of the 2-(mono- or disubstituted-6,7-dihydro-5H-pyrazo[1,2-a]pyrazolium-6-yl)thiocarbapenems from organic by-products arising from the (PNB) protecting group, which include 4-methylaniline, as well as from salts or buffer salts.

An example of removing (PNB) and (PNZ) protecting groups simultaneously in the presence of buffers and requiring chromatography for purification is shown in U.S. Pat. No. 5,602,118 which teaches a method of synthesizing (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid, by reaction of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)-butanoyl]amino}methyl)tetrahydrofuran-3-yl]thio}-7-oxo-1-azabicyclo[3.2.0]hept-2-ene-2-carboxylate with hydrogen. The reaction proceeds in the presence of palladium-on-charcoal, palladium hydroxide, platinum oxide or the like in solvent mixtures such as dioxane-water-ethanol, tetrahydrofuran-diethyl ether-buffer, tetrahydrofuran-aqueous dipotassium hydrogen phosphate-isopropanol or the like and also dioxane-water-sodium bicarbonate, dioxane-water-buffer, ethyl acetate-water-sodium bicarbonate to remove the (PNB) and/or (PNZ) protecting groups. The removal of (PNB) and/or (PNZ) groups proceeds wherein the pH is modulated by acid acceptors which includes buffers, sodium bicarbonate or potassium bicarbonate. In particular, the carbon dioxide formed from the removal of the (PNZ) protecting group is neutralized by buffers and sodium or potassium bicarbonate used in the reaction mixtures. The pH is maintained during the simultaneous removal of the (PNZ) and (PNB) blocking groups or adjusted after removal. According to U.S. Pat. No. 5,602,118 the carbapenems are isolated from the organic by-products arising from the (PNB) and/or (PNZ) protecting groups, which include 4-methylaniline, as well as from buffer salts, by chromatography.

SUMMARY OF THE INVENTION

As described in the present invention, carbapenem, (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept- 2-ene-2-carboxylic acid, is advantageously prepared from 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate by deprotecting (PNB) and (PNZ) protecting groups in a biphasic solvent mixture having an organic solvent portion and a water portion and without the use of acid acceptors for pH modulation. While not being bound by theory, simultaneous removal of the (PNZ) and (PNB) protecting groups, provides spontaneous decarboxylation forming carbon dioxide. Surprisingly, the present invention, provides a process which permits the deprotection of the (PNB) and (PNZ) protecting groups in a biphasic solvent mixture, without the use of acid acceptors for pH modulation. The process advantageously does not require a specific pH or pH adjustment during or after the simultaneous removal of the (PNZ) and (PNB) protecting groups. The carbon dioxide formed in the deprotecting of the (PNZ) group is miscible in the water portion of the biphasic solvent system as is the deprotected carbapenem, (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid and without further pH adjustment, the deprotected carbapenem is isolated from the separated water portion. Additionally, the 4-methylaniline formed in the deprotection of the (PNB) and (PNZ) groups is miscible in the organic solvent portion and does not interfere with the isolation of the deprotected carbapenem (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid from the separated water portion. A distinct advantage of the process of the invention is that (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid can be isolated in the absence of chromatography from the separated water portion.

The present invention provides a process for producing (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid, which comprises:

hydrogenation of a mixture of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate and a biphasic solvent system, said biphasic solvent system comprising an organic solvent portion and a water portion, said biphasic solvent system further characterized as not including an acid acceptor;

said hydrogenation resulting in the formation of (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid, 4-methylaniline and carbon dioxide, wherein said 4-methylaniline is miscible in the organic solvent portion of said biphasic solvent system and the carbon dioxide and (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid are miscible in the water portion of said biphasic solvent system;

upon completion of said hydrogenation, separating said water portion from said organic solvent portion and isolating (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid from said separated water portion by lyophilization or reverse osmosis.

A preferred embodiment of the present invention provides a process for producing (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid which comprises:

dissolving 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate in ethyl acetate;

adding sufficient water forming about a 1:1 ethyl acetate:water biphasic solvent system;

hydrogenation of a mixture of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate and about a 1:1 ethyl acetate:water biphasic solvent system, said biphasic solvent system further characterized as not including an acid acceptor;

said hydrogenation resulting in the formation of (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid, 4-methylaniline and carbon dioxide, wherein said 4-methylaniline is miscible in the ethyl acetate portion of said biphasic solvent system and the carbon dioxide and (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid are miscible in the water portion of said biphasic solvent system;

upon completion of said hydrogenation, separating said water portion from said ethyl acetate portion and isolating (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid from said separated water portion by lyophilization or reverse osmosis.

DESCRIPTION OF THE PREFERRED EMBODIMENTS

The following Scheme I illustrates the improved process of the present invention wherein hydrogenation of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate 1 in the presence of a catalyst and hydrogen in a biphasic solvent system, of an organic solvent and water, affords (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1- azabicyclo[3.2.0]hept-2-ene-2-carboxylic acid 2,4-methylaniline 3 and carbon dioxide.

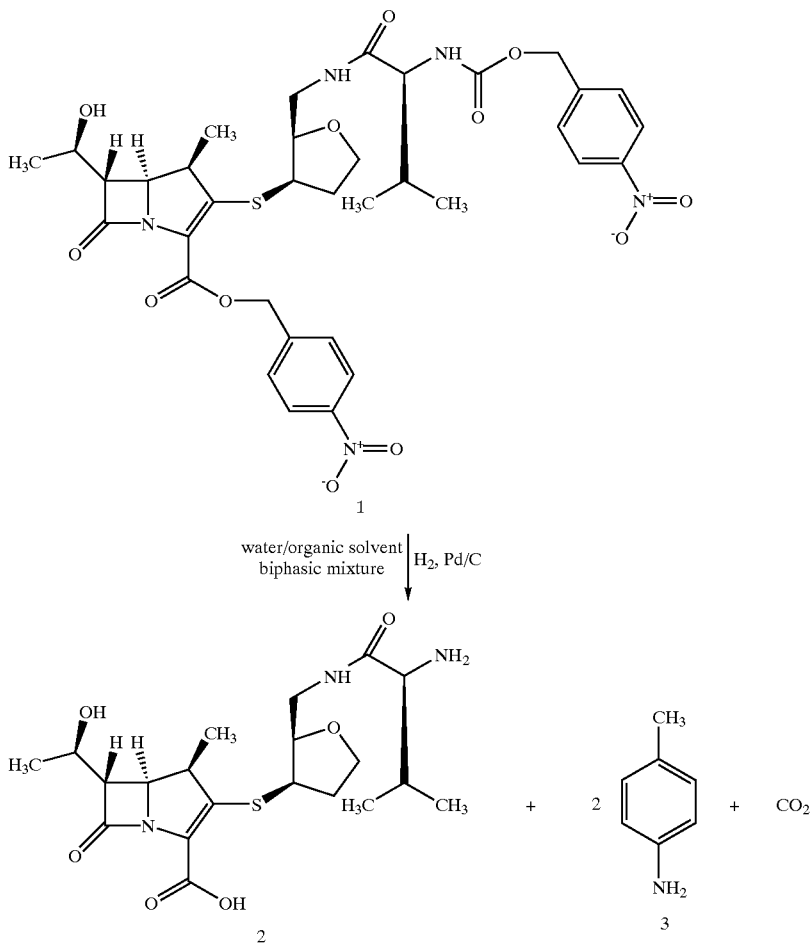

The organic portion of the biphasic solvent system is selected from the group consisting of 1-butanol, 1-pentanol, 1-hexanol, ethyl acetate and isopropyl acetate. The ratio of water portion to organic solvent portion in the biphasic system is about 1:2 (v/v) to 2:1 (v/v). Preferred is a ratio of about 1:1 (v/v), water portion to organic solvent portion. Especially preferred embodiments of the present invention utilize about 1:1 (v/v) water portion:ethyl acetate portion or about 1:1 (v/v) water portion:butanol portion. Preferred embodiments of the present invention utilize dissolving 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio }-7-oxo-1-azabicyclo[3.2.0]hept-2-ene-2-carboxylate 1 in ethyl acetate and adding sufficient water to make about a 1:1 (v/v) water:ethyl acetate biphasic mixture.

The 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate 1 is added to the biphasic solvent system of water and organic solvent in the presence of catalyst, without the addition of an acid acceptor. Suitable catalysts include palladium-on-carbon, palladium hydroxide, platinum oxide and the like. The reaction mixture is hydrogenated by shaking in a Parr hydrogenation apparatus under hydrogen pressure, until the reaction has reached completion as shown by monitoring the progress of the reaction by analytical high pressure liquid chromatography (HPLC) and cessation of hydrogen uptake. Suitably, the reaction is maintained at 20 to 30° C. for a preferred period of about 4 hours to about 24 hours at a hydrogen pressure of about 50–60 pounds-per-square inch (psi). The water portion and organic solvent portion are separated and the (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 isolated from the water portion by lyophilization or reverse osmosis.

The present invention does not use aqueous buffers or sodium or potassium bicarbonate to neutralize the carbon dioxide formed from the simultaneous reductive removal of the (PNB) and (PNZ) groups, in the presence of hydrogen, of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate 1. Chromatographic purification of the carbapenem product, (4R, 5S, 6S)-3-[[(2R,3R)-2-[[[(S)-2- amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2, in the absence of aqueous buffers or sodium or potassium bicarbonate is not required for removal of the by-products resulting from the reductive removal of the (PNB) and (PNZ) protecting groups. The improved process specifically removes the contaminate 4-methylaniline 3 giving (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 consistently as a white solid. A distinct advantage of the invention is that the 4-methylaniline 3 formed in the reaction dissolves in the organic solvent portion and the product (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 as well as the carbon dioxide formed from the deprotecting of the (PNZ) group dissolve in the water portion of the biphasic solvent mixture. The (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 can be isolated from the separated water portion, without the presence of acid acceptors, by lyophilization or reverse osmosis, thus making purification by conventional chromatographic means unnecessary.

Hydrogenation is well known in the art, usually performed in a vessel under hydrogen pressure in a solvent and in the presence of a metal catalyst.

While there are several methods known in the art for removal of water from carbapenem products which include evaporation, lyophilization and reverse osmosis, the preferred method for removal of water from (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 is lyophilization. As is known to those skilled in the art, lyophilization is a process of drying in which water is sublimed from the product after it is frozen, by applying a vacuum. Specifics of lyophilizing or freeze-drying are described in Remington's Pharmaceutical Sciences. Chapter 84, pages 1565–1567, 18$^{th}$ Edition, A. R. Gennaro, Editor, 1990, Mack Publishing Company. More preferred is reverse osmosis which rapidly removes water without increasing contaminates by decomposing (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2. A distinct advantage of reverse osmosis is the concentration of water from carbapenem antibiotics without increasing decomposition through the addition of heat. As is known to those skilled in the art, reverse osmosis employs a semipermeable membrane which will allow water to proceed through the membrane and retain the desired carbapenem for isolation. Using reverse osmosis, a solution of (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 in water, when passed through a reverse osmotic semipermeable membrane by pressure, isolates (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2, from the water. Further purification of (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 by chromatography is not necessary. Use of the above improvements allows preparation of (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid 2 in 78% to 83% or more overall yield.

The following examples are provided to illustrate the invention. The reactions of the following examples are monitored by analytical high pressure liquid chromatography (HPLC) using the following conditions:
Column: YMC-Pack ODS-AM, S-3 micron, 150×4.6 mm
Mobile Phase: Gradient A=water; B=acetonitrile

| Time | % A | % B |
|------|-----|-----|
| 0 | 98 | 2 |
| 5 | 98 | 2 |
| 25 | 75 | 25 |
| 30 | 0 | 100 |

Flow rate: 1.0 ml/minute
Temperature: 40° C.
Detection: DAD 220–300 nm
Injection solvent: acetonitrile/water; 10 μL injection; HP1090

EXAMPLE 1

(4R, 5S, 6S)-3-[[(2R,3R)-2-[[[(S)-2-Amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid To a mixture of 5.064 g of 4-nitrobenzyl (4R,5S, 6S)-6-[(1R)-1-hydroxyethyl]-4-methyl-3-{[(2R,3R)-2-({[(2S)-3-methyl-2-({[(4-nitrobenzyl)oxy]carbonyl}amino)-butanoyl]amino}methyl)tetrahydrofuran-3-yl]thio}-7-oxo-1-azabicyclo[3.2.0]hept-2-ene-2-carboxylate in 120 ml of ethyl acetate is added 5 ml of water, (about a 4% water:ethyl acetate biphasic solvent mixture) and after standing for about 5 minutes, gives a clear biphasic solvent mixture. An additional 55 ml of water is added followed by 2.5 g of 10% palladium-on-carbon. The reaction mixture is then hydrogenated in a Parr apparatus at 54 psi for 20 hours. The mixture is transferred to a separatory funnel and 100 ml of water is added. The aqueous layer is separated and the ethyl acetate layer washed with 20 ml of water. The combined aqueous layers are filtered through a pad of diatomaceous earth and the pad washed with an additional 30 ml of water. The combined aqueous layers are washed with 200 ml of ethyl acetate and lyophilized to afford 2.3 g(78%) of the desired product. MS (ES), m/z:442.3 (M+H)$^+$, 98.9% area percent pure by analytical HPLC.

EXAMPLE 2

(4R, 5S, 6S)-3-[[(2R,3R)-2-[[[(S)-2-Amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid To a mixture of 1.0 g of 4-nitrobenzyl (4R,5S,6S)-6-[(1R)-1-hydroxyethyl]-4-methyl-3-{[(2R,3R)-2-({[(2S)-3- methyl-2-({[[(4-nitrobenzyl)oxy]carbonyl}-amino)butanoyl]amino}methyl)tetrahydrofuran-3-yl]thio}-7-oxo-1-azabicyclo[3.2.0]hept-2-ene-2-carboxylate in 50 ml of 1-pentanol is added 50 ml of water followed by 0.5 g of 10% palladium-on-carbon. The reaction mixture is then hydrogenated in a Parr apparatus at 54 psi for 20 hours. The mixture is filtered through a pad of diatomaceous earth and the pad washed with an additional 40 ml of water. The filtrate is transferred to a separatory funnel, and the aqueous layer separated. The 1-pentanol layer is washed with an additional 10 ml of water. The combined aqueous layers are washed with 100 ml of ethyl acetate and lyophilized to afford 0.47 g(81%) of the desired product. MS (ES), m/z:442.3 (M+H)$^+$, 98% area percent pure by analytical HPLC.

EXAMPLE 3

(4R, 5S, 6S)-3-[[(2R,3R)-2-[[[(S)-2-Amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid To a mixture of 0.302 g of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)-butanoyl]amino}methyl)tetrahydrofuran-3-yl]thio}-7-oxo-1-azabicyclo[3.2.0]hept-2-ene-2-carboxylate in 30 ml of 1-hexanol is added 30 ml of water followed by 0.15 g of 10% palladium-on-carbon. The reaction mixture is then hydrogenated in a Parr apparatus at 54 psi for 23 hours. To the mixture is added 30 ml of water and the mixture is filtered through a pad of diatomaceous earth. The pad is washed with an additional 20 ml of water. The filtrate is transferred to a separatory funnel, the aqueous layer separated and the 1-hexanol layer is washed with 10 ml of water. The combined aqueous layers are washed with 100 ml of ethyl acetate and lyophilized to afford 0.144 g(82%) of the desired product. MS (ES), m/z:442.3 (M+H)$^+$, 99.5% area percent pure by analytical HPLC.

EXAMPLE 4

(4R, 5S, 6S)-3-[[(2R,3R)-2-[[[(S)-2-Amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid A mixture of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)-butanoyl]amino}methyl)tetrahydrofuran-3-yl]thio}-7-oxo-1-azabicyclo[3.2.0]hept-2-ene-2-carboxylate (0.200 g), 50% wet 10% palladium on carbon (0.256 g), 1-butanol (20 ml) and water (20 ml) is hydrogenated in a Parr apparatus at 56 psi for 8 hours. The catalyst is then removed by filtration through diatomaceous earth and washed with 2×6 ml of water. The 1-butanol layer is extracted once with 6 ml of water. The combined aqueous solution (ca. 38 ml) is extracted twice with 2×10 ml of isopropyl acetate, concentrated under reduced pressure below 28° C. to ca. 20 ml and lyophilized to give 97.1 mg (83.0%) of the desired product as a slightly tan solid. MS (ES), m/z:442.3 (M+H)$^+$; rotation $[\alpha]_D^{25}$ +42±1° (c 0.84, H$_2$O); purity by analytical HPLC (100%).

We claim:

1. A process for producing (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid, which comprises:

hydrogenation of a reaction mixture of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate and a biphasic solvent system, said biphasic solvent system comprising an organic solvent portion and a water portion, said biphasic solvent system further characterized as not including an acid acceptor in addition to 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]-amino}methyl)tetrahydrofuran-3-yl]thio}-7-oxo-1-azabicyclo[3.2.0]hept-2-ene-2-carboxylate and (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid;

said hydrogenation resulting in the formation of (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid, 4-methylaniline and carbon dioxide, wherein said 4-methylaniline is miscible in the organic solvent portion of said biphasic solvent system and the carbon dioxide and (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid are miscible in the water portion of said biphasic solvent system;

upon completion of said hydrogenation, separating the water portion from said organic solvent portion and isolating (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid from said separated water portion by lyophilization or reverse osmosis.

2. A process according to claim 1 wherein said biphasic solvent system comprises about 1:2 (v/v) to about 2:1 (v/v) water portion:organic solvent portion.

3. A process according to claim 1 wherein the reaction is carried out in a biphasic solvent mixture of about 1:1 (v/v) water portion:organic solvent portion.

4. A process according to claim 1 wherein said organic solvent portion is selected from the the group consisting of 1-butanol, 1-pentanol, 1-hexanol, ethyl acetate and isopropyl acetate.

5. A process according to claim 4 wherein the organic solvent portion is 1-butanol.

6. A process according to claim 4 wherein the organic solvent portion is 1-pentanol.

7. A process according to claim 4 wherein the organic solvent portion is 1-hexanol.

8. A process according to claim 4 wherein the organic solvent portion is ethyl acetate.

9. A process according to claim 4 wherein the organic solvent portion is isopropyl acetate.

10. A process as claimed in claim 1 wherein the (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo [3.2.0]hept-2-ene-2-carboxylic acid is isolated by lyophilization of the separated water portion.

11. A process as claimed in claim 1 wherein the (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid is isolated by reverse osmosis of the separated water portion.

12. A process according to claim 1 wherein the hydrogenation is performed in the presence of a catalyst selected from the group consisting of palladium-on-carbon, palladium hydroxide, and platinum oxide.

13. A process for producing (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo [3.2.0]hept-2-ene-2-carboxylic acid which comprises:

dissolving 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate in ethyl acetate;

adding sufficient water forming about a 1:1 ethyl acetate:water biphasic solvent system;

hydrogenation of a reaction mixture of 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate and about a 1:1 ethyl acetate:water biphasic solvent system, said biphasic solvent system further characterized as not including an acid acceptor in addition to 4-nitrobenzyl (4R,5S,6S)-6-[(1R)-1-hydroxyethyl]-4-methyl-3-{[(2R,3R)-2-({[(2S)-3-methyl-2-({[(4-nitrobenzyl)oxy]carbonyl}amino)butanoyl]amino}methyl)tetrahydrofuran-3-yl]thio}-7-oxo-1-azabicyclo[3.2.0]hept-2-ene-2-carboxylate and (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid;

said hydrogenation resulting in the formation of (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid, 4-methylaniline and carbon dioxide, wherein said 4-methylaniline is miscible in the ethyl acetate organic solvent portion of said biphasic solvent system and the carbon dioxide and (4R, 5S, 6S)-3-[[(2R,3R)-2-[[[(S)-2-amino-3-methyl-1-oxobutyl]amino]methyl]-tetrahydro-3-furanyl]thio]-6-[(R)-1-hydroxyethyl]-4-methyl-7-oxo-1-azabicyclo[3.2.0]hept-2-ene-2-carboxylic acid are miscible in the water portion of said biphasic solvent system;

upon completion of said hydrogenation, separating the water portion from said ethyl acetate portion and isolating (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid from said separated water portion by lyophilization or reverse osmosis.

14. A process as claimed in claim 13 wherein the (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid is isolated by lyophilization of the separated water portion.

15. A process as claimed in claim 13 wherein the (4R, 5S, 6S)-3-[[(2R,3R)-2-[[[(S)-2-amino-3-methyl-1-oxobutyl]amino]methyl]tetrahydro-3-furanyl]thio]-6-[(R)-1-hydroxyethyl]-4-methyl-7-oxo-1-azabicyclo[3.2.0]hept-2-ene-2-carboxylic acid is isolated by reverse osmosis of the separated water portion.

16. A process according to claim 13 wherein the hydrogenation is performed in the presence of a catalyst selected from the group consisting of palladium-on-carbon, palladium hydroxide, and platinum oxide.

\* \* \* \* \*